United States Patent [19]

Koike et al.

[11] 4,211,723

[45] Jul. 8, 1980

[54] PROCESS FOR PRODUCING CHLOROSULFONYLBENZOYLCHLORIDE

[75] Inventors: Wataro Koike; Takahiro Kimoto, both of Shizuoka; Sadayoshi Matsui, Shimizu, all of Japan

[73] Assignee: Ihara Chemical Industry Co., Ltd., Tokyo, Japan

[21] Appl. No.: 917,255

[22] Filed: Jun. 20, 1978

Related U.S. Application Data

[63] Continuation of Ser. No. 674,178, Apr. 6, 1976, abandoned.

[30] Foreign Application Priority Data

Jun. 11, 1975 [JP] Japan ................... 50-70311
Nov. 19, 1975 [JP] Japan ................... 50-138988

[51] Int. Cl.$^2$ ................... C07C 63/14; C07C 143/52
[52] U.S. Cl. ................... 260/544 K; 260/544 S; 260/544 N
[58] Field of Search ........... 260/543 R, 544 K, 544 S, 260/544 N

[56] References Cited

U.S. PATENT DOCUMENTS 3,184,506  5/1965  Parker et al. ................... 260/544 K
3,857,841  5/1974  Keil ................... 260/544 K Primary Examiner—Joseph E. Evans
Attorney, Agent, or Firm—Oblon, Fisher, Spivak, McClelland & Maier

[57] ABSTRACT

Chlorosulfonylbenzoylchloride having the formula

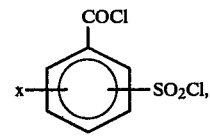

wherein X is hydrogen, halogen or nitro is prepared by reacting phosgene with an aromatic sulfocarboxylic acid having the formula

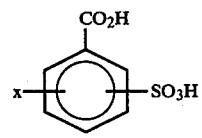

or an alkali metal salt or alkaline earth metal salt thereof in the presence of dimethylformamide.

9 Claims, No Drawings

PROCESS FOR PRODUCING CHLOROSULFONYLBENZOYLCHLORIDE

This is a continuation of application Ser. No. 674,178, filed Apr. 6, 1976, now abandoned.

BACKGROUND OF THE INVENTION

The present invention relates to a process for producing chlorosulfonylbenzoylchloride which is useful as an intermediate for medicines, food additives and agricultural chemicals.

DESCRIPTION OF THE PRIOR ART

The following is a description of several processes known to produce chlorosulfonylbenzoylchloride.

(1) Chlorosulfonylbenzoylchloride is produced by chlorinating an alkali metal salt or ammonium salt of an aromatic sulfocarboxylic acid with phosphorus pentachloride or a mixture of phosphorus pentachloride and phosphorus oxychloride. (Berichte, 31, 1649; ibid. Vol. 31, page 1654; ibid Vol. 55, page 1506; J. Am. Chem. Soc., 13, page 261; ibid. Vol. 30, page 487; ibid Vol. 23, page 235; ibid Vol. 23, page 239; ibid. Vol. 25, page 204 and ibid. Vol. 50, page 196)

(2) Benzotrichloride is chlorosulfonated with chlorosulfonic acid to yield m-chlorosulfonylbenzotrichloride, and the product is heated to obtain m-chlorosulfonylbenzoylchloride. (U.S. Pat. No. 3,290,370)

(3) Benzoic acid is chlorosulfonated to yield m-chlorosulfonyl benzoic acid and the product is chlorinated with thionylchloride to yield m-chlorosulfonylbenzoyl chloride. (B.P. No. 921,520) However, the conventional processes have several disadvantages and are not suitable for industrial procedures. In the conventional process (1), which uses phosphorus pentachloride or a mixture of phosphorus pentachloride and phosphorus oxychloride as the chlorinating agent, the chlorinating agent is expensive and phosphorus oxychloride or metaphosphoric acid is produced as a byproduct the presence of which makes it mandatory to purify chlorosulfonylbenzoylchloride by distillation. Moreover, the phosphorus oxychloride and metaphosphoric acid are sources of pollution.

Other disadvantages of the process are that the process gives rise to substantial coloring of the reaction product, and the chlorosulfonylbenzoylchloride is produced in low yields. In process (2) on the other hand in which benzotrichloride is chlorosulfonated and heated, it is difficult to prevent hydrolysis of the object product, and it is difficult to produce chlorosulfonylbenzoylchloride in high yield.

In conventional process (3) in which benzoic acid is chlorosulfonated and then the product is chlorinated with thionylchloride, sulfur dioxide gas is generated which causes serious pollution problem.

In chlorosulfonation processes (2) and (3), it is not possible to produce o- or p-chlorosulfonylbenzoylchloride having which have a chlorosulfonyl group at the o- or p- position to the chloroformyl group.

SUMMARY OF THE INVENTION

Accordingly, one object of the present invention is to economically produce chlorosulfonylbenzoylchloride on an industrial scale.

Another object of the invention is to produce chlorosulfonylbenzoylchloride in high purity and high yield.

These objects and other objects can be attained by providing a process for producing chlorosulfonylbenzoylchloride having the formula

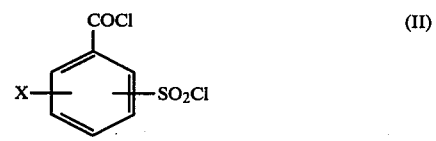

wherein X represents hydrogen, halogen or nitro, by reacting phosgene with an aromatic sulfocarboxylic acid having the formula

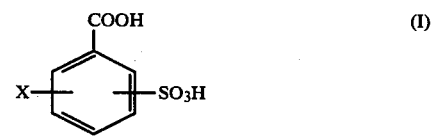

or an alkali metal salt or alkaline earth metal salt thereof, in the presence of dimethylformamide.

DETAILED DESCRIPTION OF THE PREFERRED EMBODIMENTS

A study has been conducted on methods for producing chlorosulfonylbenzoylchloride in high purity and high yield to overcome the disadvantages of the conventional processes.

As result, it has been found that both the carboxyl group and sulfonic acid group of an aromatic sulfocarboxylic acid can be simultaneously chlorinated by reacting phosgene with an aromatic sulfocarboxylic acid or an alkali metal salt or alkaline earth metal salt thereof in the presence of the dimethylformamide. By this procedure a chlorosulfonylbenzoylchloride of high purity can be produced in high yield.

In the method of the invention, as shown by the following reaction, dimethylformamide reacts with phosgene in the reaction (1) and reaction product (III) as used as the chlorinating agent for the aromatic sulfocarboxylic acid (a) or the alkali metal salt of aromatic sulfocarboxylic acid (b) (c) and (d) or the alkaline earth metal salt of aromatic sulfocarboxylic acid (e) (f) and (g). In each of reaction schemes (2), (3) and (4), chlorosulfonylbenzoylchloride II is produced and dimethylformamide is recovered.

Reaction (1):

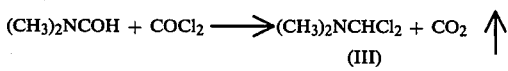

Reaction (2):

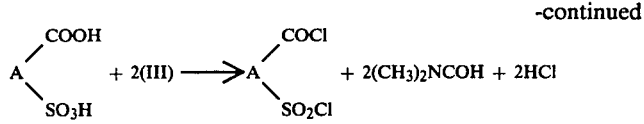

(a)

Reaction (3):

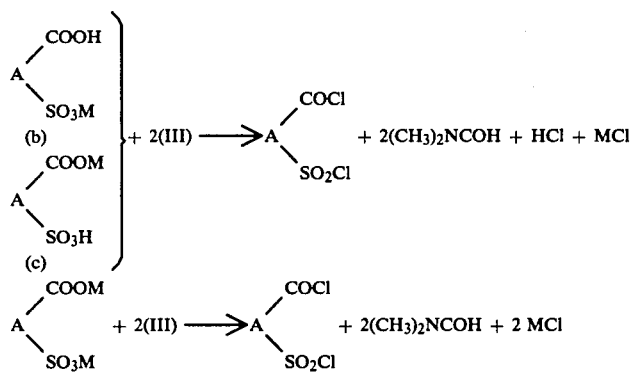

Reaction (4):

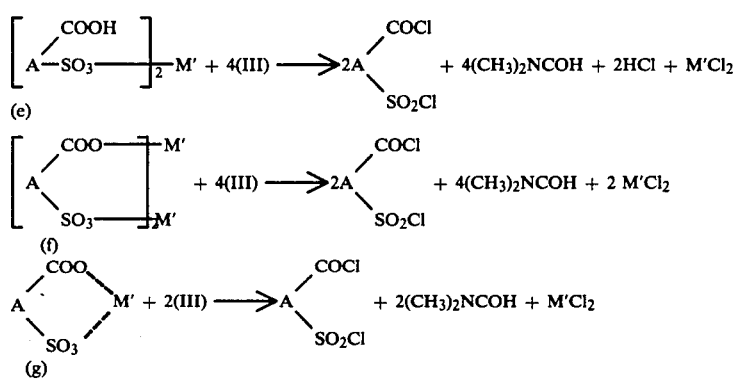

In the formulae of the reactions above A represents a benzene ring which can be substituted by a halogen atom or a nitro group; M represents an alkali metal and M' represents an alkaline earth metal.

When an o-sulfocarboxylic acid or the metal salt thereof, wherein the sulfonic acid group is placed in an ortho position to the carboxylic group in formula (I), is used as a starting material, a mixture of o-chlorosulfonylbenzoylchloride and dichlorotolylsultone is produced as shown in the following reaction.

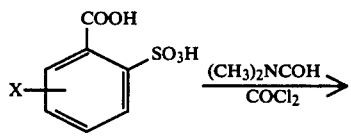

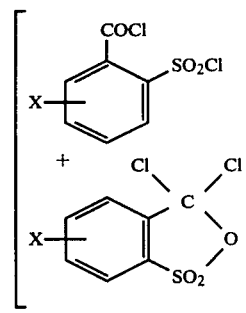

The mixture of o-chlorosulfonylbenzoylchloride and dichlorotolylsultone can be used as the starting materials in a subsequent step without any separation and purification.

For example, in accordance with the process of the invention, phosgene reacts with o-sulfobenzoic acid or the alkali metal salt or alkaline earth metal salt thereof in the presence of dimethylformamide. The resulting reaction mixture of o-chlorosulfonylbenzoylchloride and dichlorotolylsultone is mixed with an alcohol to esterify o-chlorosulfonylbenzoylchloride. The mixture of the ester of o-chlorosulfonylbenzoylchloride and dichlorotolylsultone is mixed with ammonia to prepare the ammonium salt of o-sulfobenzimide.

The o-sulfobenzimide which is useful as an intermediate for medicinal agents, (sweetener for diabetics), food additives (sweeteners) or agricultural chemicals can be produced by treating the ammonium salt of the o-sulfobenzimide with a mineral acid.

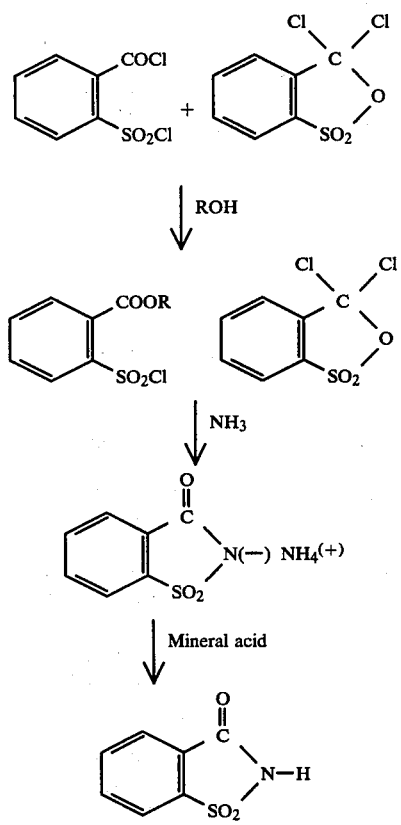

In the process of the invention, the aromatic sulfocarboxylic acid of formula (I) or an alkali metal salt or alkaline earth metal salt thereof is used.

The sulfonic acid group and X in formula (I) can be bonded at a desired position on the benzene ring. Reference symbol X includes hydrogen, nitro or a halogen such as chlorine, bromine, iodine or fluorine.

Aromatic sulfocarboxylic acid (I) can be produced by the oxidation of toluenesulfonic acid or the sulfonation of an aromatic carboxylic acid. The alkali metal salts or alkaline earth metal salts of aromatic sulfocarboxylic acids include alkali metal salts (b) (c) and (d) Reaction (3) and the alkaline earth metal salts (e) (f) and (g) in Reaction (4) or mixtures thereof.

Suitable alkali metals include sodium and potassium, and the alkaline earth metals include magnesium, calcium, barium and the like.

For example, the mono-metal salts (b) and (e) in Reaction (3) and (4) can be produced by salting out of the aromatic sulfocarboxylic acid (I). The dimetal salts (d) (f) and (g) in Reactions (3) and (4) can be produced by neutralizing the aromatic sulfocarboxylic acid (I) with an alkali metal hydroxide or an alkaline earth metal hydroxide.

The reaction of aromatic sulfocarboxylic acid (I) or alkali metal salt or alkaline earth metal salt thereof with phosgene in the presence of dimethylformamide is usually conducted in an inert organic solvent. The amount of dimethylformamide used in the reaction is in a range of less than 1 mole usually 0.01–0.3 mole, preferably 0.03–0.1 mole per mole of the aromatic sulfocarboxylic acid (I) or a salt thereof. It is possible to use excess dimethylformamide, although it is not economical. The amount of phosgene employed is more than an equivalent amount (stoichiometric amount) preferably 5–20% excess. Phosgene can be directly introduced into the reaction system and can also be used by dissolving it in an inert solvent such as carbon tetrachloride, toluene or the like. Suitable inert organic solvents used in the reaction include aliphatic hydrocarbons such as cyclohexane, n-hexane and the like; halohydrocarbons such as chloroform, carbon tetrachloride, trichloroethylene, tetrachloroethylene and the like aromatic hydrocarbons such as benzene, toluene, xylene, chlorobenzene and the like; ethers such as diethyl ether, dibutyl ether, dioxane and the like; ketones such as acetone, methylethyl ketone, methylisopropyl ketone and the like; nitriles such as acetonitrile, propionitrile, and the like; and esters such as ethyl acetate, butyl acetate and the like.

The reaction temperature and the reaction time are chosen depending upon the type of aromatic sulfocarboxylic acid, the alkali metal salt or alkaline earth metal salt thereof and the speed at which phosgene is fed. The reaction temperature is usually in a range of 20°–150° C., preferably 40°–100° C.

The reaction time is usually in a range of 5–7 hours and can be less than 8 hours.

In the process of the invention as shown in the reactions hydrogen chloride, an alkali metal chloride or an alkaline earth metal chloride are produced as by-products.

The hydrogen chloride can be easily recovered by using any type of desired absorption tower. The metal chlorides can be easily separated by conventional processes.

The characteristics and advantages of the process of the invention will now be illustrated.

(1) Both of the carboxyl group and the sulfonic acid group of the aromatic sulfocarboxylic acid can be simultaneously chlorinated under mild conditions. Accordingly, it is unnecessary to remove the reaction intermediate mixture and to purify it. The chlorosulfonylbenzoylchloride can be produced in high yield in one step without decomposition of the product.

(2) In accordance with the process of the invention, chlorosulfonylbenzoylchloride, wherein the chlorosulfonyl group is bonded at any desired o-, m-, or p- position to the chloroformyl group can be produced by appropriate selection of the starting material.

(3) The chlorosulfonylbenzoylchloride produced by the process of the invention is of high purity. Accordingly it is unnecessary to further purify the compound and the product can be directly used as the starting material for the following step.

(4) Phosgene which is economically and readily available, is used as the chlorinating agent. Accordingly, an advantage of the present process as an industrial process over other conventional processes using expensive chlorinating agents such as phosphorus pentachloride, phosphorus oxychloride and thionylchloride is the use of phosgene.

The invention will be further illustrated by certain examples.

EXAMPLE 1

Into a four necked flask equipped with a stirrer, a thermometer, a condenser and a dropping funnel, 20.2 g of o-sulfobenzoic acid, 75 ml of carbon tetrachloride, and 0.22 g of dimethylformamide were charged. The mixture was stirred at 70°-75° C. and 75 ml of a carbon tetrachloride solution of phosgene (phosgene content of 30% W/V) were added dropwise and the reaction was conducted for 7 hours. After the reaction, nitrogen gas was injected to remove excess phosgene. The reaction solution was concentrated to remove the solvent and the product was distilled under reduced pressure whereby 21.8 g of a distilled product having a boiling point of 142°-146° C./4 mmHg (yield 91.2%) were obtained.

Gas chromatographic analysis confirmed that the distilled product was a mixture of o-chlorosulfonylbenzoylchloride and dichlorotolylsultone.

Preparation of o-sulfobenzimide

A 20 g amount of the mixture of o-chlorosulfonylbenzoylchloride and dichlorotolylsultone was added dropwise to 40 ml of methanol with stirring at 15°-20° C. and the mixture was stirred and reacted for 1 hour. After the reaction, the reaction mixture was added dropwise to 35 g of 8% ammonia water with stirring at 20°-25° C., and the reaction mixture was kept for one night. Then, methanol was removed by distillation from the reaction mixture under a reduced pressure, and hydrochloric acid was added to the residual product to adjust pH to 1-2. The precipitated crystals were filtered and washed with water and dried, to obtain 14.3 g of white crystals of o-sulfobenzimide having a melting point of 227°-228° C. (yield of 93%).

EXAMPLE 2

In accordance with the process of Example 1, the reaction of p-sulfobenzoic acid with phosgene was conducted by mixing 20.2 g of p-sulfobenzoic acid in 75 ml of carbon tetrachloride and 0.22 g of dimethylformamide with 75 ml of a carbon tetrachloride solution of phosgene (phosgene content of 30% W/V).

After the reaction, excess phosgene was removed and the reaction mixture was concentrated and the precipitated crystals were filtered to obtain 22.0 g of white crystals of p-chlorosulfonylbenzoylchloride having a melting point of 56°-58° C. (yield of 92%).

EXAMPLE 3

In a flask (four necked) equipped with a stirrer, a thermometer, a condenser, a phosgene inlet, 24.0 g of monopottasium salt of m-sulfobenzoic acid,

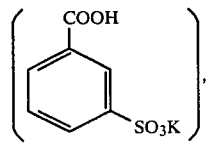

150 ml of toluene, and 0.22 g of dimethylformamide were charged. The mixture was stirred at 80° C., and 23 g of phosgene was introduced during 4 hours. The reaction was further continued under a reflux at 80°-90° C. for 3 hours with stirring. After the reaction, nitrogen gas was injected to remove exess of phosgene.

The reaction mixture was filtered to remove potassium chloride, and the filtrate was condensed and distilled under a reduced pressure to obtain 22.8 g of a colorless liquid of m-chlorosulfonylbenzoylchloride having a boiling point of 146°-148° C./5 mmHg. (yield of 95.2%).

EXAMPLE 4

In accordance with the process of Example 3, the reaction of calcium salt of p-sulfobenzoic acid

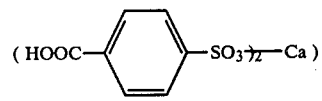

with phosgene by mixing 24.1 g of calcium salt of p-sulfobenzoic acid, 150 ml of toluene, 0.35 g of dimethylformamide and 23 g of phosgene. After the reaction, nitrogen gas was injected to remove excess of phosgene. The reaction mixture was filtered to remove potassium chloride and the filtrate was condensed and the precipitated crystals were filtered and recrystallized from petroleum ether whereby 21.3 g of white crystals of p-chlorosulfonylbenzoylchloride having a melting point of 57°-58° C. (yield of 89.0%) were obtained.

COMPARATIVE TEST

Into a four necked flask equipped with a stirrer, a thermometer and a condenser, 24.0 g of the monopotassium salt of m-sulfobenzoic acid, and 20.8 g of phosphorus pentachloride were charged and the mixture was stirred and reacted at 100°-110° C. for 5 hours. After the reaction, phosphorus oxychloride was removed by distillation and the product was extracted with ether washed with water and dried. The ether solution was condensed and dried whereby 18.6 g of m-chlorosulfonylbenzoylchloride, were obtained. (yield of 78.0%).

EXAMPLE 5

In accordance with the process of Example 4, each of the aromatic sulfocarboxylic acids, alkali metal salts and akaline earth metal salts thereof as shown in Table I were reacted with phosgene in an inert solvent in the presence of dimethylformamide whereby each of the respective chlorosulfonylbenzoylchloride compounds were obtained. The results are shown in Table 1.

Table 1

| | Starting Material | | Solvent & | Amount | React. | React. |
|---|---|---|---|---|---|---|
| Expt. No. | Compound | Amount (g) | Amount of Hosgene (g) | Amount (ml) | of DMF (g) | Temp. (°C.) | Hour (hr) |

Table 1-continued

| Expt. No. | Compound | | | Solvent | | | |
|---|---|---|---|---|---|---|---|
| 1 | 4-Cl, 3-SO₃Na benzoic acid | 25.9 | 23.0 | Chlorobenzene 150 | 0.3 | 80 | 6 |
| 2 | [4-Cl, 3-SO₃-benzoic acid]₂Ba | 30.4 | 23.5 | Xylene 150 | 0.3 | 90 | 7 |
| 3 | 4-Br, 2-SO₃K benzoic acid K salt | 35.7 | 22.0 | Propionitrile 150 | 0.25 | 80 | 7 |
| 4 | 5-NO₂, 2-SO₃K benzoic acid K salt | 32.3 | 22.5 | Methylethylketone 150 | 0.4 | 75 | 8 |

Note:
DMF: Dimethylformamide

Table 1'

| | | Product | | |
|---|---|---|---|---|
| Expt. No. | Compound | Amount (g) | Yield (%) | m.p. (°C.) |
| 1 | 4-Cl benzoyl chloride-3-SO₂Cl | 25.4 | 93.0 | 40–42 |
| 2 | 4-Cl benzoyl chloride-3-SO₂Cl | 24.0 | 88.0 | 40–42 |
| 3 | 4-Br benzoyl chloride-2-SO₂Cl + cyclic CCl₂ adduct | 29.3 | 92.0 | 83–89 |
| 4 | 5-NO₂ benzoyl chloride-2-SO₂Cl + cyclic CCl₂ adduct | 25.3 | 89.0 | 51–57 |

We claim:
1. A process for producing chlorosulfonylbenzoyl-chloride having the formula

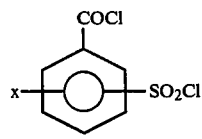

wherein x is hydrogen, halogen, or nitro, which comprises reacting phosgene with an aromatic sulfocarboxylic acid having the formula

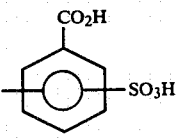

or an alkali metal salt or akaline earth metal salt thereof in the presence of 0.01–0.3 mole of dimethylformamide per mole of said aromatic sulfocarboxylic acid.

2. The process according to claim 1, wherein the reaction is conducted in an inert solvent.

3. The process according to claim 1, wherein the aromatic sulfocarboxylic acid is o-, m- or p- sulfobenzoic acid.

4. The process according to claim 1, wherein the aromatic sulfocarboxylic acid is o-, m-, or p- halosulfobenzoic acid or nitrosulfobenzoic acid.

5. The process according to claim 1, wherein the alkali metal salt or alkaline earth metal salt of the aromatic sulfocarboxylic acid is a monometal salt or dimetal salt thereof.

6. The process of claim 1, wherein the alkaline earth metal of said alkaline earth metal salt is calcium, barium or magnesium and the alkali metal of said alkali metal is sodium or potassium.

7. The process of claim 1, wherein the temperature of said reaction ranges from 20°–150° C.

8. The process of claim 1, wherein the time of reaction is less than 8 hours.

9. The process of claim 2, wherein said insert solvent is a hydrocarbon, a halohydrocarbon, an aromatic hydrocarbon, an ether, a ketone, a nitrile or an ester.

* * * * *